(12) United States Patent
Udupa et al.

(10) Patent No.: US 10,111,624 B2
(45) Date of Patent: Oct. 30, 2018

(54) MEASURING ELECTRODE IMPEDANCE IN AN IMPEDANCE MEASUREMENT CIRCUIT

(71) Applicant: Texas Instruments Incorporated, Dallas, TX (US)

(72) Inventors: Anand Hariraj Udupa, Bangalore (IN); Jagannathan Venkataraman, Bangalore (IN); Hussam Ahmed, Calicut (IN); Sandeep Kesrimal Oswal, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 15/936,029

(22) Filed: Mar. 26, 2018

(65) Prior Publication Data

US 2018/0214084 A1  Aug. 2, 2018

Related U.S. Application Data

(63) Continuation of application No. 14/683,338, filed on Apr. 10, 2015.

(30) Foreign Application Priority Data

Apr. 11, 2014  (IN) .......................... 1926/CHE/2014

(51) Int. Cl.
*A61B 5/00* (2006.01)
*A61B 5/053* (2006.01)

(52) U.S. Cl.
CPC ............ *A61B 5/6898* (2013.01); *A61B 5/053* (2013.01); *A61B 5/7221* (2013.01); *A61B 5/0535* (2013.01); *A61B 5/0537* (2013.01); *A61B 2560/0468* (2013.01)

(58) Field of Classification Search
CPC ..... A61B 5/053; A61B 5/0537; A61B 5/6898; G01N 33/48728; G01N 33/5438
USPC .......................................... 683/692
See application file for complete search history.

(56) References Cited

U.S. PATENT DOCUMENTS

| | | | | |
|---|---|---|---|---|
| 3,851,641 | A | * | 12/1974 | Toole ................... A61B 5/0537 324/650 |
| 3,871,359 | A | * | 3/1975 | Pacela .................. A61B 5/0408 324/692 |
| 4,459,995 | A | * | 7/1984 | Conners ................. G01R 17/10 324/154 R |

(Continued)

OTHER PUBLICATIONS

Prosecution History from U.S. Appl. No. 14/683,338, dated Apr. 10, 2015 to Dec. 26, 2017, 157 pp.

(Continued)

*Primary Examiner* — Christopher McAndrew
(74) *Attorney, Agent, or Firm* — Gregory J. Albin; Charles A. Brill; Frank D. Cimino

(57) ABSTRACT

The disclosure provides a circuit for impedance measurement. The circuit includes an excitation source coupled between a first set of input switches. An impedance network is coupled between the first set of input switches and a first set of output switches. The impedance network includes a body impedance and a plurality of electrode impedances. A sense circuit is coupled to the first set of output switches. The sense circuit measures the body impedance and at least one electrode impedance of the plurality of electrode impedances.

11 Claims, 3 Drawing Sheets

(56) References Cited

U.S. PATENT DOCUMENTS

| | | | | |
|---|---|---|---|---|
| 5,187,096 | A * | 2/1993 | Giaever | G01N 33/4836 |
| | | | | 204/403.01 |
| 7,443,175 | B2 * | 10/2008 | Podhajsky | G01N 27/221 |
| | | | | 324/663 |
| 7,941,210 | B2 * | 5/2011 | Matthiessen | A61B 5/0536 |
| | | | | 324/600 |
| 2002/0079910 | A1 * | 6/2002 | Fukuda | A61B 5/05 |
| | | | | 324/692 |
| 2008/0012582 | A1 * | 1/2008 | Jang | A61B 5/0531 |
| | | | | 324/692 |
| 2008/0036475 | A1 * | 2/2008 | Waki | A61B 5/0537 |
| | | | | 324/692 |
| 2008/0275361 | A1 | 11/2008 | Loriga et al. | |
| 2010/0004548 | A1 * | 1/2010 | Rytky | A61B 5/04288 |
| | | | | 600/509 |
| 2010/0016809 | A1 * | 1/2010 | Grober | A61M 5/158 |
| | | | | 604/272 |
| 2010/0102834 | A1 * | 4/2010 | Shyu | H03K 17/962 |
| | | | | 324/692 |
| 2011/0169511 | A1 * | 7/2011 | Nordin | G01N 33/5005 |
| | | | | 324/692 |
| 2015/0305648 | A1 | 10/2015 | Udupa et al. | |
| 2017/0265771 | A1 | 9/2017 | Udupa et al. | |

OTHER PUBLICATIONS

AFE4300, Low-Cost, Integrated Analog Front-End for Weight-Scale and Body Composition Measurement, available at http://www.ti.com/lit/ds/symlink/afe4300.pdf, Jun. 2013 (30 pages).

AFE4300 Development Guide, User's Guide, available at http://www.ti.com/lit/ug/2bau201.pdf, Aug. 2012 (46 pages).

* cited by examiner

MEASURING ELECTRODE IMPEDANCE IN AN IMPEDANCE MEASUREMENT CIRCUIT

CROSS REFERENCES TO RELATED APPLICATIONS

This application is a continuation of U.S. patent application Ser. No. 14/683,338 filed Apr. 10, 2015, and claims the benefit of India Provisional Patent Application Serial No. 1926/CHE/2014, filed Apr. 11, 2014, both of which are incorporated herein by reference in their entirety.

TECHNICAL FIELD

The present disclosure is generally related to an impedance measurement circuit, and more particularly to measuring electrode impedance in the impedance measurement circuit.

BACKGROUND

In biomedical engineering, bio-impedance is the response of a living organism to externally applied electric current. Bio-impedance or body impedance is a measure of the opposition to the flow of that electric current through the tissues, the opposite of the electrical conductivity. The measurement of the body impedance of humans and animals has proved useful as a non-invasive method for measuring blood flow and body composition.

One method of measuring the body impedance is using electrodes. A fixed excitation current (either AC or DC) is injected in a human body through a pair of excitation electrodes. A pair of sense electrodes is coupled to the human body. A sense circuit measures a voltage difference across the sense electrodes. The voltage difference corresponds to the impedance of the human body.

An impedance associated with each electrode of the pair of excitation electrodes and the pair of sense electrodes, affects the accuracy of the measured body impedance. Traditional devices does not take into consideration the high range of impedance associated with the electrodes, because these devices provide large electrodes which allow a large area of contact between the electrode and the human body. However, modern consumer devices like cell phones need to take into consideration the impedance associated with the electrodes.

Existing solutions compensate for such high range of electrode impedance by compromising on the sense circuit. In one existing solution, the excitation current is reduced significantly to compensate for the high range of impedance of the electrodes. However, a reduction in excitation current also reduces the voltage difference generated across the sense electrodes. This leads to inaccuracies in the measurement of the body impedance.

SUMMARY

According to an aspect of the disclosure, a circuit is disclosed. The circuit includes an excitation source coupled between a first set of input switches. An impedance network is coupled between the first set of input switches and a first set of output switches. The impedance network includes a body impedance and a plurality of electrode impedances. A sense circuit is coupled to the first set of output switches. The sense circuit measures the body impedance and at least one electrode impedance of the plurality of electrode impedances.

BRIEF DESCRIPTION OF THE VIEWS OF DRAWINGS

DETAILED DESCRIPTION OF THE EMBODIMENTS

Figure 1:
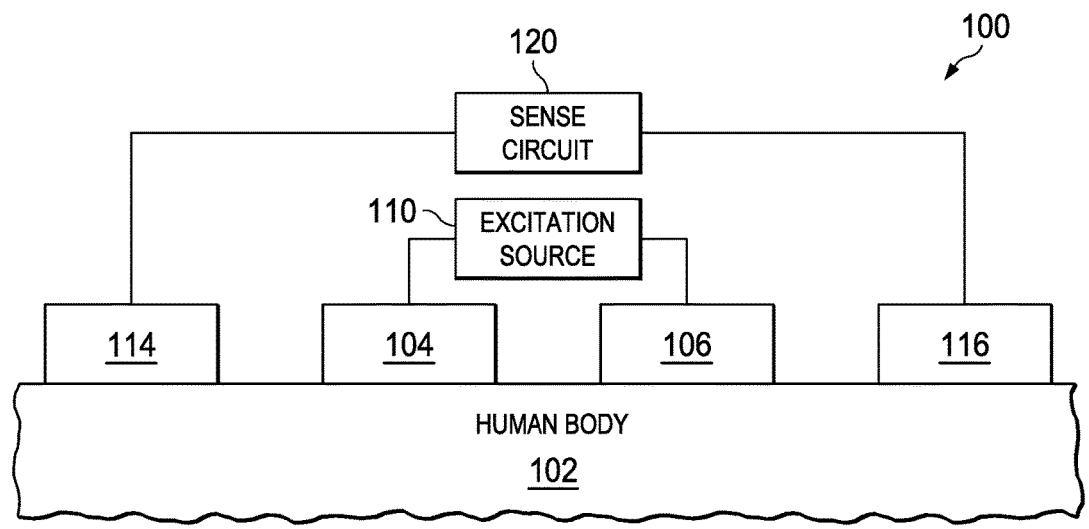
FIG. 1 is a block diagram of an impedance measurement circuit, in which various embodiments can be implemented.

FIG. 1 is a block diagram of an impedance measurement circuit 100, in which various embodiments can be implemented. The impedance measurement circuit 100 is coupled to a human body 102. The impedance measurement circuit 100 includes an excitation source 110. The excitation source 110 is coupled between a pair of excitation electrodes 104 and 106. The excitation electrodes 104 and 106 are coupled to the human body 102. A pair of sense electrodes 114 and 116 is also coupled to the human body 102. A sense circuit 120 is coupled between the pair of sense electrodes 114 and 116.

The operation of the impedance measurement circuit 100 illustrated in FIG. 1 is explained now. The excitation source 110 generates an AC or a DC signal. In one example, the excitation source 110 generates a high frequency AC current which is injected in the human body 102 through the pair of excitation electrodes 104 and 106. The AC current causes a voltage difference between the pair of sense electrodes 114 and 116. The sense circuit 120 measures this voltage difference. This voltage difference is related to the resistivity of the human body 102 between the pair of sense electrodes 114 and 116.

An impedance of the human body 102 is defined as the ratio of the voltage difference between the pair of sense electrodes 114 and 116 and the AC current that is injected in the human body 102. However, a number of factors affect the accuracy of the measured impedance of the human body. These factors include, but not limited to, connectivity of the pair of excitation electrodes 104 and 106 with the human body 102, and connectivity of the pair of sense electrodes 114 and 116 with the human body 102.

The impedance between the electrode and the human body 102 could be much higher than the impedance of the human body. As a result, it becomes difficult to determine if the readings by the impedance measurement circuit 100 are accurate. Also, it is difficult to determine the cause of error in the impedance measurement circuit 100.

Figure 2:
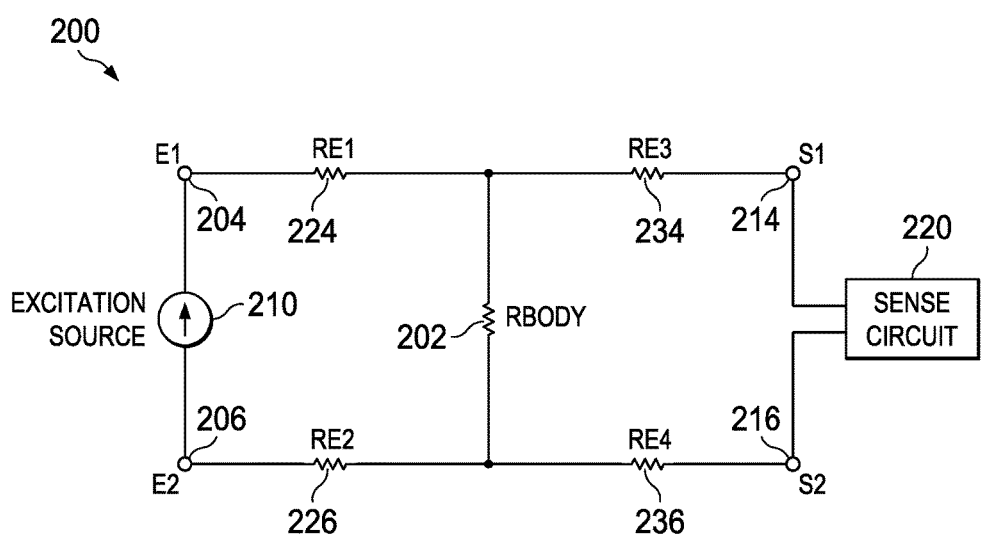
FIG. 2 is a schematic of an impedance measurement circuit.

FIG. 2 is a schematic of an impedance measurement circuit 200. The impedance measurement circuit 200 is a schematic of impedance measurement circuit 100, illustrated in FIG. 1. The impedance measurement circuit 200 includes an excitation source 210 similar to the excitation source 110.

The excitation source 210 is coupled between a first excitation terminal E1 204 and a second excitation terminal E2 206. The first excitation terminal E1 204 corresponds to the excitation electrode 104, and the second excitation terminal E2 206 corresponds to the excitation electrode 106. An impedance associated with the excitation electrode 104 is represented by a first input electrode impedance RE1 224, and an impedance associated with the excitation electrode 106 is represented by a second input electrode impedance RE2 226.

An impedance associated with the human body 102 is represented as a body impedance RBODY 202. A sense circuit 220 is coupled between a first sense terminal S1 214 and a second sense terminal S2 216. The first sense terminal S1 214 corresponds to the sense electrode 114, and the second sense terminal S2 216 corresponds to the sense electrode 116.

An impedance associated with the sense electrode 114 is represented as a first output electrode impedance RE3 234, and an impedance associated with the sense electrode 116 is represented as a second output electrode impedance RE4 236. The first output electrode impedance RE3 234 is coupled to the first input electrode impedance RE1 224, the body impedance RBODY 202 and the first sense terminal S1 214.

The second output electrode impedance RE4 236 is coupled to the second input electrode impedance RE2 226, the body impedance RBODY 202 and the second sense terminal S2 216.

The operation of the impedance measurement circuit 200 illustrated in FIG. 2 is explained now. The excitation source 210 generates and AC or a DC signal. In one example, the excitation source 210 generates a high frequency AC current. The AC current is injected in the human body through the pair of excitation electrodes. The AC current traverses from the first excitation terminal E1 204 to the second excitation terminal E2 206 through the body impedance RBODY 202.

A voltage difference is created between the first sense terminal S1 214 and the second sense terminal S2 216. The sense circuit 220 measures this voltage difference. The voltage difference provided a measure of the body impedance RBODY 202. The body impedance RBODY 202 is a resistivity of the human body 102 between the first sense terminal S1 214 and the second sense terminal S2 216.

The body impedance RBODY 202 is defined as the ratio of the voltage difference between the first sense terminal S1 214 and the second sense terminal S2 216, and the AC current that is generated by the excitation source 210. However, a number of factors affect the accuracy of the measured body impedance RBODY 202. These factors include, but not limited to, connectivity of the pair of excitation electrodes with the human body and connectivity of the pair of sense electrodes with the human body.

Whenever an electrode is not in proper contact with the human body, it results in increase in the magnitude of the electrode impedance. For example, when the excitation electrode 104 is not in proper contact with the human body 102, it results in increase in magnitude of the first input electrode impedance RE1 224. This results in inaccurate measurement of the body impedance RBODY 202 by the sense circuit 220.

Figure 3:
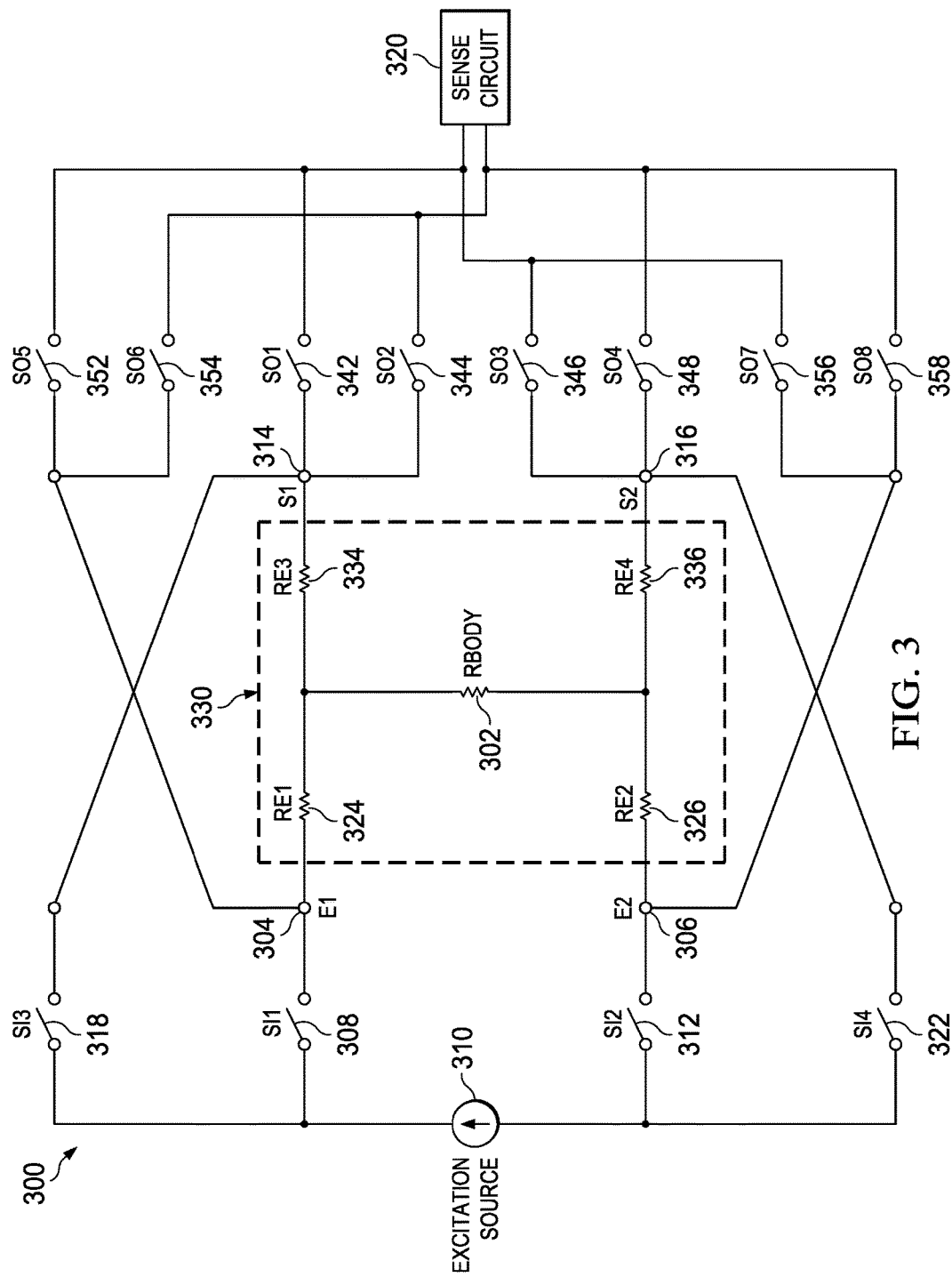
FIG. 3 is a schematic of a circuit, according to an embodiment.

FIG. 3 is a schematic of a circuit 300, according to an embodiment. The circuit 300, in one example, in an impedance measurement circuit. The circuit 300 includes an excitation source 310, an impedance network 330 and a sense circuit 320. The excitation source 310 is coupled between a first set of input switches, which include a first input switch SI1 308 and a second input switch SI2 312.

The impedance network 330 is coupled between the first set of input switches and a first set of output switches. The first set of output switches includes a first output switch SO1 342, a second output switch SO2 344, a third output switch SO3 346 and a fourth output switch SO4 348. The sense circuit 320 is coupled to the first set of output switches.

A second set of input switches includes a third input switch SI3 318 and a fourth input switch SI4 322. The second set of input switches is coupled in parallel to the first set of input switches. The excitation source 310 is coupled between the second set of input switches i.e. the excitation source is coupled between the third input switch SI3 318 and the fourth input switch SI4 322.

A second set of output switches includes a fifth output switch SO5 352, a sixth output switch SO6 354, a seventh output switch SO7 356 and an eighth output switch SO8 358. The second set of output switches is coupled between the impedance network 330 and the sense circuit 320. The impedance network 330 includes a body impedance RBODY 302 and a plurality of electrode impedances. The plurality of electrode impedance includes a first input electrode impedance RE1 324, a second input electrode impedance RE2 326, a first output electrode impedance RE3 334 and a second output electrode impedance RE4 336.

The first input electrode impedance RE1 324 is coupled to a first excitation terminal E1 304. The second input electrode impedance RE2 326 is coupled to a second excitation terminal E2 306. The body impedance RBODY 302 is coupled between the first input electrode impedance RE1 334 and the second input electrode impedance RE2 326. The first output electrode impedance RE3 334 is coupled to a first sense terminal S1 314, and the second output electrode impedance RE4 336 is coupled to a second sense terminal S2 316.

The first excitation terminal E1 304 corresponds to a first excitation electrode (similar to the excitation electrode 104), and the second excitation terminal E2 306 corresponds to a second excitation electrode (similar to the excitation electrode 106). An impedance associated with the first excitation electrode is represented by the first input electrode impedance RE1 324, and an impedance associated with the second excitation electrode is represented by a second input electrode impedance RE2 326.

An impedance associated with the human body 102 is represented as a body impedance RBODY 302. The first sense terminal S1 314 corresponds to a first sense electrode (similar to the sense electrode 114), and the second sense terminal S2 316 corresponds to a second sense electrode (similar to the sense electrode 116). An impedance associated with the first sense electrode is represented as the first output electrode impedance RE3 334, and an impedance associated with the second sense electrode is represented as the second output electrode impedance RE4 336.

The first input switch SI1 308 is coupled between the excitation source 310 and the first excitation terminal E1 304. The second input switch SI2 312 is coupled between the excitation source 310 and the second excitation terminal E2 306. The third input switch SI3 318 is coupled between the excitation source 310 and the first sense terminal S1 314. The fourth input switch SI4 322 is coupled between the excitation source and the second sense terminal S2 316.

The first output switch SO1 342 and the second output switch SO2 344 are coupled between the first sense terminal S1 314 and the sense circuit 320. The third output switch SO3 346 and the fourth output switch SO4 348 are coupled between the second sense terminal S2 316 and the sense circuit 320. The fifth output switch SO5 352 and the sixth output switch SO6 354 are coupled between the first excitation terminal E1 304 and the sense circuit 320.

The seventh output switch SO7 356 and the eighth output switch SO8 358 are coupled between the second excitation terminal E2 306 and the sense circuit 320. In one version, the circuit 300 is part of a medical diagnostic device. In another version, the circuit 300 is integrated in a consumer electronic device such as, but not limited to, a mobile, a PDA (personal digital assistant), and a smartphone. In yet another version, the circuit 300 is part of a device used in industrial application. The circuit 300 may include one or more additional components known to those skilled in the relevant art and are not discussed here for simplicity of the description.

The operation of the circuit 300 illustrated in FIG. 3 is explained now. The excitation source 310 generates and AC or a DC signal. In one example, the excitation source 310 generates a high frequency AC current. The AC current is injected in the human body through the pair of excitation electrodes. The AC current traverses from the first excitation terminal E1 304 to the second excitation terminal E2 306 through the body impedance RBODY 302.

The sense circuit 320 measures the body impedance RBODY 302, and at least one electrode impedance of the plurality of electrode impedances. The sense circuit 320 measures the body impedance RBODY 302 when the first input switch SI1 308, the second input switch SI2 312, the first output switch SO1 342 and the fourth output switch SO4 348 are closed.

The sense circuit 320 measures the first input electrode impedance RE1 324 when the first input switch SI1 308, the second input switch SI2 312, the second output switch SO2 344 and the fifth output switch SO5 352 are closed. The sense circuit 320 measures the second input electrode impedance RE2 326 when the first input switch SI1 308, the second input switch SI2 312, the third output switch SO3 346 and the eighth output switch SO8 358 are closed.

The sense circuit 320 measures the first output electrode impedance RE3 334 when the third input switch SI3 318, the fourth input switch SI4 322, the first output switch SO1 342 and the sixth output switch SO6 354 are closed. The sense circuit 320 also measures the second output electrode impedance RE4 336 when the third input switch SI3 318, the fourth input switch SI4 322, the fourth output switch SO4 348 and the seventh output switch SO7 356 are closed.

A various combinations of the switches closed, and a corresponding impedance measured by the sense circuit 320 is illustrated in Table 1.

TABLE 1

| Switches Closed | Impedance Measured |
| --- | --- |
| SI1, SI2, SO1, SO4 | RBODY |
| SI1, SI2, SO5, SO8 | RBODY + RE1 + RE2 |
| SI3, SI4, SO5, SO8 | RBODY |
| SI3, SI4, SO1, SO4 | RBODY + RE3 + RE4 |
| SI1, SI2, SO5, SO4 | RBODY + RE1 |
| SI1, SI2, SO1, SO8 | RBODY + RE2 |
| SI3, SI4, SO1, SO8 | RBODY + RE3 |
| SI3, SI4, SO5, SO4 | RBODY + RE4 |
| SI1, SI2, SO5, SO2 | RE1 |
| SI1, SI2, SO3, SO8 | RE2 |
| SI3, SI4, SO1, SO6 | RE3 |
| SI3, SI4, SO7, SO4 | RE4 |

The sense circuit 320 generates an indication signal when at least one electrode impedance of the plurality of electrode impedances is above a defined threshold. For example, when the impedance of first input electrode impedance RE1 324 is above the defined threshold, the sense circuit 320 generates the indication signal. In one example, the defined threshold is provided by a user. In another example, the defined threshold is a maximum impedance of a human body.

In one version, when the circuit 300 is part of a medical diagnostic device, the indication signal is used by a user to understand that at least one electrode of the plurality of electrodes is not making proper contact with the human body. In the above example, the indication signal would signify that the first excitation electrode (whose impedance is represented as RE1 324) is not making proper contact with the human body.

The sense circuit 320 determines an accurate value of the body impedance RBODY 302 when each electrode impedance of the plurality of electrode impedances is below the defined threshold. The sense circuit 320 determines the accurate value of the body impedance RBODY 302 from the measured body impedance RBODY 302 and the plurality of electrode impedances.

Thus, when each of the first input electrode impedance RE1 324, the second input electrode impedance RE2 326, the first output electrode impedance RE3 334 and the second output electrode impedance RE4 336 are below the defined threshold, the sense circuit 320 determines the accurate value of the body impedance RBODY 302. The sense circuit 320 determines the accurate value of the body impedance RBODY 302 using the measured body impedance RBODY 302, the first input electrode impedance RE1 324, the second input electrode impedance RE2 326, the first output electrode impedance RE3 334 and the second output electrode impedance RE4 336.

The accurate value of the body impedance RBODY 302 is more precise than the body impedance RBODY 302 measured by the sense circuit 320. The accurate value of the body impedance RBODY 302 is a more precise measurement of the impedance of the human body by the sense circuit 320. Thus, the circuit 300 provides a technique to measure various impedances in the impedance network 330, which is used by the sense circuit 320 for determination of the accurate value of the body impedance RBODY 302 which is more precise than the measured body impedance RBODY 302. By measuring various impedances in the impedance network 330, the circuit 300 provides a reliable and accurate means for measuring the impedance of the body.

Figure 4:
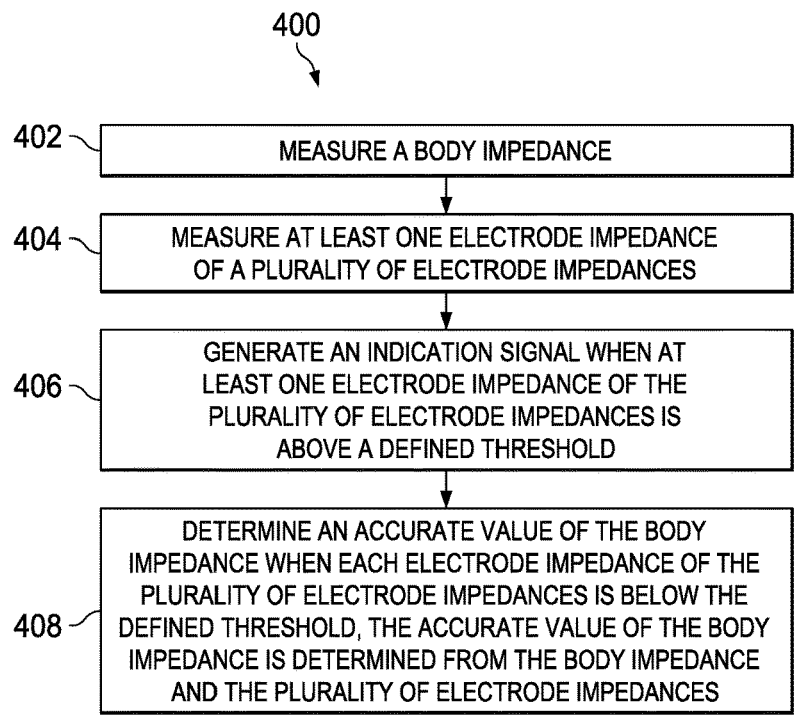
FIG. 4 illustrates a method of impedance measurement, according to an embodiment.

FIG. 4 illustrates a method 400 of impedance measurement, according to an embodiment. At step 402, a body impedance is measured. An excitation source generates and AC or a DC current signal. In one example, the excitation source generates a high frequency AC current. The AC current is injected in the human body through the pair of excitation electrodes.

In circuit 300 the body impedance RBODY 302 is measured when the first input switch SI1 308, the second input switch S12 312, the first output switch SO1 342 and the fourth output switch SO4 348 are closed. In one version, a body impedance represents an impedance of a human body. At step 404, at least one electrode impedance of the plurality of electrode impedances is measured.

In circuit 300, at least one of the first input electrode impedance RE1 324, the second input electrode impedance RE2 326, the first output electrode impedance RE3 334 and the second output electrode impedance RE4 336 is measured. An indication signal is generated when at least one electrode impedance of the plurality of electrode impedances is above a defined threshold, at step 406.

In one example, the defined threshold is provided by a user. In another example, the defined threshold is a maximum impedance of the human body. The indication signal signifies that at least one electrode of the plurality of electrodes is not making proper contact with the human body. At step 408, an accurate value of the body impedance is determined when each electrode impedance of the plurality of electrode impedances is below the defined threshold. The accurate value of the body impedance is determined from the measured body impedance and the plurality of electrode impedances.

For example, in circuit 300, when each of the first input electrode impedance RE1 324, the second input electrode impedance RE2 326, the first output electrode impedance RE3 334 and the second output electrode impedance RE4 336 is below the defined threshold, the sense circuit 320 determines the accurate value of the body impedance RBODY 302. The sense circuit 320 determines the accurate value of the body impedance RBODY 302 using the measured body impedance RBODY 302, the first input electrode impedance RE1 324, the second input electrode impedance RE2 326, the first output electrode impedance RE3 334 and the second output electrode impedance RE4 336.

The accurate value of the body impedance RBODY 302 is more precise than the measured body impedance RBODY 302. The accurate value of the body impedance RBODY 302 is a more precise measurement of the impedance of the human body. The method 400 provides a reliable technique to measure impedance of the human body. The measurement of electrode impedances provides a unique way of fault detection, and a user is provided the indication signal for making better contact with the electrodes.

Figure 5:
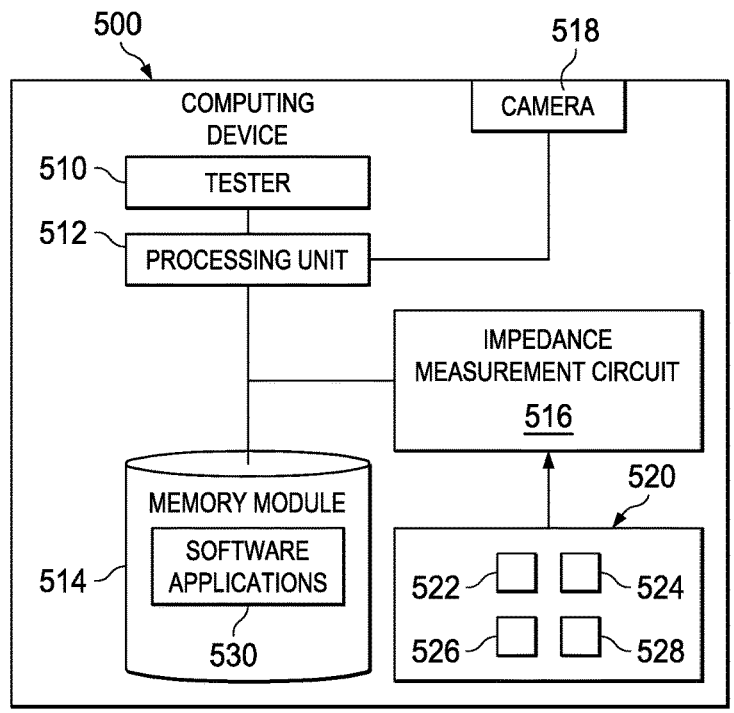
FIG. 5 illustrates a computing device, according to an embodiment.

FIG. 5 illustrates a computing device 500, according to an embodiment. The computing device 500 is, or is incorporated into, a mobile communication device, such as a mobile phone, a personal digital assistant, a transceiver, a personal computer, or any other type of electronic system. The computing device 500 may include one or more additional components known to those skilled in the relevant art and are not discussed here for simplicity of the description.

In some embodiments, the computing device 500 comprises a megacell or a system-on-chip (SoC) which includes a processing unit 512 such as a CPU (Central Processing Unit), a memory module 514 (e.g., random access memory (RAM)) and a tester 510. The processing unit 512 can be, for example, a CISC-type (Complex Instruction Set Computer) CPU, RISC-type CPU (Reduced Instruction Set Computer), or a digital signal processor (DSP).

The memory module 514 (which can be memory such as RAM, flash memory, or disk storage) stores one or more software applications 530 (e.g., embedded applications) that, when executed by the processing unit 512, performs any suitable function associated with the computing device 500. The tester 510 comprises logic that supports testing and debugging of the computing device 500 executing the software applications 530.

For example, the tester 510 can be used to emulate a defective or unavailable component(s) of the computing device 500 to allow verification of how the component(s), were it actually present on the computing device 500, would perform in various situations (e.g., how the component(s) would interact with the software applications 530). In this way, the software applications 530 can be debugged in an environment which resembles post-production operation.

The processing unit 512 typically comprises memory and logic which store information frequently accessed from the memory module 514. A camera 518 is coupled to the processing unit 512. The computing device 500 includes an impedance measurement circuit 516. The impedance measurement circuit 516 is coupled to the processing unit 512 and the memory module 514. The impedance measurement circuit 516 is coupled to an electrode chip 520.

The electrode chip 520 includes a first excitation electrode 522, a second excitation electrode 524, a first sense electrode 526 and a second sense electrode 528. In one version, the electrode chip 520 is integrated in the computing device 500. In another version, the first excitation electrode 522, the second excitation electrode 524, the first sense electrode 526 and the second sense electrode 528 are positioned in the computing device 500 appropriately based on the application of the computing device 500. In yet another version, the electrode chip is separate from the computing device 500, and may communicate with the computing device 500 by a wired/wireless medium. In a different version, the electrode chip 520 includes a plurality of electrodes. The operation of the impedance measurement circuit 516 is similar the operation of the circuit 300 illustrated in FIG. 3.

The first excitation terminal E1 304 in circuit 300 corresponds to the first excitation electrode 522, and the second excitation terminal E2 306 corresponds to the second excitation electrode 524. An impedance associated with the first excitation electrode 522 is represented by the first input electrode impedance RE1 324, and an impedance associated with the second excitation electrode 524 is represented by a second input electrode impedance RE2 326.

The first sense terminal S1 314 corresponds to the first sense electrode 526, and the second sense terminal S2 316 corresponds to the second sense electrode 528. An impedance associated with the first sense electrode 526 is represented as the first output electrode impedance RE3 334, and an impedance associated with the second sense electrode 528 is represented as the second output electrode impedance RE4 336.

The impedance measurement circuit 516 includes a sense circuit similar to the sense circuit 320. The sense circuit generates an indication signal when at least one electrode impedance of the plurality of electrode impedances is above a defined threshold. For example, when the first input electrode impedance RE1 324 is above the defined threshold, the sense circuit 320 generates the indication signal.

In one version, when the computing device 500 is part of a medical diagnostic device, the indication signal is used by a user to understand that at least one electrode of the plurality of electrodes is not making proper contact with the human body. In the above example, the indication signal would signify that the first excitation electrode 522 is not making proper contact with the human body. In another example, the impedance measurement circuit 516 is used for fault detection, in which case the indication signal is used by a user to understand that the combination of fingers used for touching electrodes is not correct. For example, in one case, when the user is touching both the first excitation electrode 522, and the second excitation electrode 524 with fingers of same hand, the sense circuit generates an indication signal.

The sense circuit determines an accurate value of the body impedance when each electrode impedance of the plurality of electrode impedances is below the defined threshold. The sense circuit 320 determines the accurate value of the body impedance RBODY 302 from the body impedance RBODY 302 and the plurality of electrode impedances.

The accurate value of the body impedance is a more precise measurement of the impedance of the human body by the sense circuit. Thus, the impedance measurement circuit 516 provides a reliable technique for measuring body impedance.

The foregoing description sets forth numerous specific details to convey a thorough understanding of the invention. However, it will be apparent to one skilled in the art that the invention may be practiced without these specific details.

Well-known features are sometimes not described in detail in order to avoid obscuring the invention. Other variations and embodiments are possible in light of above teachings, and it is thus intended that the scope of invention not be limited by this Detailed Description, but only by the following Claims.

The invention claimed is:

1. A circuit comprising:
an excitation source;
a sense circuit;
a first electrode;
a second electrode;
a first switch coupled between a terminal of the excitation source and the first electrode;
a second switch coupled between the first electrode and a terminal of the sense circuit;
a third switch coupled between the terminal of the excitation source and the second electrode; and
a fourth switch coupled between the second electrode and the terminal of the sense circuit,
wherein the sense circuit is configured to close both the first switch and the second switch during measurement of an impedance.

2. The circuit of claim 1, wherein the first and second electrodes are included in a plurality of electrodes, and wherein the sense circuit is configured to generate an indication signal when at least one electrode impedance of a plurality of electrode impedances is above a defined threshold.

3. The circuit of claim 2, wherein the sense circuit is configured to determine a value of a body impedance when each electrode impedance of the plurality of electrode impedances is below the defined threshold.

4. The circuit of claim 1, wherein the sense circuit is configured to close the first switch and open the second switch during measurement of an impedance.

5. A circuit comprising:
an excitation source;
a sense circuit;
a first electrode;
a second electrode;
a first switch coupled between a terminal of the excitation source and the first electrode;
a second switch coupled between the first electrode and the sense circuit; and
a third switch coupled between the terminal of the excitation source and the second electrode,
wherein the sense circuit is configured to close both the first switch and the second switch during measurement of an impedance.

6. A circuit comprising:
an excitation source;
a sense circuit;
a first electrode;
a second electrode;
a first switch coupled between the excitation source and the first electrode;
a second switch coupled between the first electrode and a terminal of the sense circuit; and
a third switch coupled between the second electrode and the terminal of the sense circuit,
wherein the sense circuit is configured to close both the first switch and the second switch during measurement of an impedance.

7. A circuit comprising:
an excitation source;
a sense circuit;
a first electrode;
a second electrode;
a first switch coupled between the excitation source and the first electrode;
a second switch coupled between the first electrode and a first terminal of the sense circuit;
a third switch coupled between the first electrode and a second terminal of the sense circuit;
a fourth switch coupled between the second electrode and the first terminal of the sense circuit; and
a fifth switch coupled between the second electrode and the second terminal of the sense circuit,
wherein the sense circuit is configured to close both the first switch and the second switch during measurement of an impedance.

8. A circuit comprising:
an excitation source;
a sense circuit;
a first electrode;
a first switch coupled between the excitation source and the first electrode;
a second switch coupled between the first electrode and a first terminal of the sense circuit; and
a third switch coupled between the first electrode and a second terminal of the sense circuit,
wherein the sense circuit is configured to close both the first switch and the second switch during measurement of an impedance.

9. A computing device comprising:
a processing unit;
a memory module coupled to the processing unit; and
an impedance measurement circuit coupled to the processing unit and the memory module, the impedance measurement circuit comprising:
an excitation source;
a sense circuit;
a first electrode;
a second electrode;
a first switch coupled between a terminal of the excitation source and the first electrode; and
a second switch coupled between the first electrode and a terminal of the sense circuit;
a third switch coupled between the terminal of the excitation source and the second electrode; and
a fourth switch coupled between the second electrode and the terminal of the sense circuit,
wherein the sense circuit is configured to close both the first switch and the second switch during measurement of an impedance.

10. The computing device of claim 9, wherein the first and second electrodes are first and second excitation electrodes in a plurality of electrodes, the plurality of electrodes further including first and second sense electrodes.

11. The computing device of claim 9, wherein the sense circuit is configured to:
generate an indication signal when at least one electrode impedance of a plurality of electrode impedances is above a defined threshold; and
determine a value of the body impedance when each electrode impedance of the plurality of electrode impedances is below the defined threshold.

* * * * *